United States Patent
Borbás et al.

(10) Patent No.: US 10,699,446 B2
(45) Date of Patent: Jun. 30, 2020

(54) PROCESS AND MEASURING SYSTEM FOR DATA ACQUISITION AND PROCESSING IN SOFT-TOMOGRAPHY STUDIES

(71) Applicant: Pécsi Tudományegyetem, Pécs (HU)

(72) Inventors: Károly Borbás, Pécs (HU); Tibor Kiss, Pécs (HU); Mihály Klincsik, Pécs (HU); Zoltán Kvasznicza, Mánfa (HU); Kálmán Máthé, Pécs (HU); Csaba Vér, Pécs (HU); Zoltán Vizvári, Pécs (HU); Péter Odry, Előszállás (HU)

(73) Assignee: Pécsi Tudományegyetem, Pécs (HU)

( * ) Notice: Subject to any disclaimer, the term of this patent is extended or adjusted under 35 U.S.C. 154(b) by 195 days.

(21) Appl. No.: 16/062,319

(22) PCT Filed: Dec. 14, 2016

(86) PCT No.: PCT/HU2016/050062
§ 371 (c)(1),
(2) Date: Jun. 14, 2018

(87) PCT Pub. No.: WO2017/125770
PCT Pub. Date: Jul. 27, 2017

(65) Prior Publication Data
US 2018/0374244 A1    Dec. 27, 2018

(30) Foreign Application Priority Data

Dec. 14, 2015  (HU) .................... 1500616

(51) Int. Cl.
*G06T 11/00* (2006.01)
*A61B 5/053* (2006.01)
(Continued)

(52) U.S. Cl.
CPC .......... *G06T 11/006* (2013.01); *A61B 5/0536* (2013.01); *G01R 27/04* (2013.01);
(Continued)

(58) Field of Classification Search
CPC ... A61B 5/0536; A61B 5/0073; A61B 5/4547; A61B 5/0084; A61B 5/7228; A61B 8/13;
(Continued)

(56) References Cited

U.S. PATENT DOCUMENTS

| 7,548,320 B2 * | 6/2009 | Chan ............ A61B 3/102 356/497 |
| 8,115,934 B2 * | 2/2012 | Boppart ......... A61B 5/0066 356/479 |

(Continued)

FOREIGN PATENT DOCUMENTS

| CA | 3007977 | 7/2017 |
| JP | 2019505773 | 2/2019 |

OTHER PUBLICATIONS

H. Gagnon, et al. ; "A Resistive Mesh Phantom for Assessing the Performance of EIT Systems" published in 2009. in the magazine entitled IEEE Transactions on Biomedical Engineering in vol. 57, Issue 9, 10 pages.

(Continued)

*Primary Examiner* — Aklilu K Woldemariam
(74) *Attorney, Agent, or Firm* — Fitch, Even, Tabin & Flannery LLP (57) ABSTRACT

A measuring system (100) for data acquisition in soft-field tomography analysis of an object (62) includes transmitting units (63-*i*), receiving units (65-*j*), measuring units (67-*j*), an excitation unit having an alive point ("hot spot"; 81) and a ground point ("cold spot"; 82), a measuring data acquisition unit (85), and a control unit (90). In the operational state, the control unit (90) controls the excitation unit and the measuring data acquisition unit (85); the excitation unit connects to a transmitting unit (63-*i*), one at a time, to drive the transmitting units (63-*i*). Transmitting units (63-*i*) and the receiving units (65-*j*) couple, one by one, with the object (62) to excite and detect response upon the excitation field, (Continued)

wherein the receiving units (65-j) connect together in pairs to form measuring circuits to characterize the detected response quantitatively by measurement data.

22 Claims, 3 Drawing Sheets

(51) Int. Cl.
    *G01R 27/04* (2006.01)
    *G01R 27/14* (2006.01)
(52) U.S. Cl.
    CPC ............ *G01R 27/14* (2013.01); *G06T 11/005* (2013.01); *G06T 2207/10072* (2013.01)
(58) Field of Classification Search
    CPC ...... A61B 5/053; A61B 5/7253; G01R 27/04; G01R 27/14; G01R 33/3875; G01R 33/243; G01R 33/3415; G01R 33/481; G01R 33/4828; G01R 33/543; G01R 33/561; G01R 33/583; G06T 11/005; G06T 2207/20101; G06T 2207/30084; G06T 2207/10072; G06T 11/008; G06T 11/006; G01B 9/02004; G01B 9/02014; G01B 9/02083; G01B 9/02091; G06F 30/23; B21B 13/142; F27B 14/14; F27D 2099/004
    USPC ........... 382/128, 276; 356/51, 479; 324/310, 324/318, 600, 693
    See application file for complete search history.

(56) References Cited

U.S. PATENT DOCUMENTS

| | | | | |
|---|---|---|---|---|
| 8,378,682 | B2* | 2/2013 | Subbarao | G01R 33/48 324/307 |
| 8,593,154 | B2 | 11/2013 | Ross | |
| 2006/0228009 | A1* | 10/2006 | Fidrich | G06T 7/12 382/128 |
| 2010/0127705 | A1 | 5/2010 | Scharfetter | |
| 2011/0163770 | A1 | 7/2011 | Mahalingam | |
| 2012/0161782 | A1* | 6/2012 | Ross | A61B 5/0073 324/600 |
| 2012/0242350 | A1* | 9/2012 | Sundaresan | A61B 5/0536 324/629 |
| 2013/0006558 | A1* | 1/2013 | Langoju | G06T 11/006 702/65 |
| 2013/0013239 | A1* | 1/2013 | Ross | A61B 5/0073 702/66 |
| 2013/0109962 | A1* | 5/2013 | Uutela | A61B 5/0536 600/427 |
| 2013/0225985 | A1* | 8/2013 | Ross | A61B 5/0536 600/425 |

OTHER PUBLICATIONS

Written Opinion of the International Searching Authority dated May 7, 2017 for PCT/HU2016/050062; 7 pages.
International Search Report for PCT/HU2016/050062 dated May 7, 2017; 2 pages.
Notification of International Preliminary Report on Patentability for PCT/HU2016/050062, dated Jan. 25, 2018; 16 pages.
Tushar Kanti Bera et al, "Studying the resistivity imaging of chicken tissue phantoms with different current patterns in Electrical Impedance Tomography (EIT)", Measurement, Institute of Measurement and Control. London, GB, vol. 45, No. 4, doi:10.1016/J.MEASUREMENT.2012.01.002, ISSN 0263-2241, (Jan. 7, 2012), pp. 663-682, (Jan. 15, 2012), XP028459730 [X] 1-16,18,20 * section 2; pp. 664-671.
Mcewan A et al, "A review of errors in multi-frequency EIT instrumentation", Physiological Measurement, Institute of Physics Publishing, Bristol, GB, (Jul. 1, 2007), vol. 28, No. 7, doi:10.1088/0967-3334/28/7/S15, ISSN 0967-3334, pp. S197-S215, XP020120800 [A] 1-20 * p. S204 * * p. S206-p. S210 *.
Mcewan A et al, "Design and calibration of a compact multi-frequency EIT system for acute stroke imaging", Physiological Measurement, Institute of Physics Publishing, Bristol, GB, (May 1, 2006), vol. 27, No. 5, doi:10.1088/0967-3334/27/5/S17, ISSN 0967-3334, pp. S199-S210, XP020105769.

* cited by examiner

(prior art)

PROCESS AND MEASURING SYSTEM FOR DATA ACQUISITION AND PROCESSING IN SOFT-TOMOGRAPHY STUDIES

CROSS REFERENCE TO RELATED APPLICATIONS

This patent application is the national phase of PCT/HU2016/050062 filed Dec. 14, 2016, which claims the benefit of Hungarian Patent Application No. P1500616 filed Dec. 14, 2015.

BACKGROUND

The present invention relates to the completion of nondestructive soft-field tomography analysis of an object under study. In particular, the object of the present invention is a data acquisition and processing method, as well as a measuring system for the soft-field tomographic mapping of the internal structure of objects under study, specifically objects with inhomogeneous material distribution. The present invention, particularly, provides a data acquisition/processing method, as well as a measuring system serving as a basis for a soft-field tomography analysis and/or an imaging method. The method and measuring system according to the invention may be used advantageously in industrial tomography processes, for nondestructive structural analysis of different materials (e.g. live wood), and in medical diagnostic methods (such as e.g. body-fat analysis, in particular, obesity measurement, or oncological examinations performed, in particular, for mapping cell proliferation, and other similar methods). Accordingly, here and from now on the term "object" may substantially refer to any material under study ranging from industrial articles through structures found in nature to organs/tissues forming parts of a human or animal body.

The problem of analyzing or visualizing the internal structure of a three-dimensional object without destroying it is present in numerous fields of technology and science. Said analysis or visualization can be achieved by means of transilluminating the object by a radiation that is mostly transmitted by the object under study, but also absorbed by it to a sufficient extent to obtain a 'silhouette' of its internal structure (imaging). If the internal structure of the object under study is nearly two dimensional or is not too complex, such silhouettes can be directly interpreted. In more complex cases, however, images captured in only a few directions are not sufficient for revealing the internal structure. Reconstructing the internal structure of an object (e.g. the material distribution, inhomogeneity, internal defects of said object, etc.) from two dimensional silhouettes is generally a rather complicated task, therefore, it is a common practice to take so-called tomographic sectional images. This means that a planar section of the three dimensional object is studied by capturing one dimensional images in different directions along the plane and then attempting the reconstruction of the planar structure from said images. In this context, the term "structure" refers to the spatial variation/distribution of the absorption of the radiation applied—thus, tomography refers to the solution of this two-dimensional problem. For such, so-called hard-field tomography methods, X-ray radiation or acoustic radiation (e.g. ultrasound) is commonly used as the transilluminating radiation.

Besides the above discussed methods, so-called soft-field tomography methods are also known. Such a soft-field tomography method is, without completeness, amongst others the electrical resistance tomography (ERT), electrical capacitance tomography (ECT), electrical impedance tomography (EIT) and acoustic impedance tomography (AIT), which inspection methods are directed to the mapping and measuring of the spatial variance of the internal properties of the object under study, such as the electrical/dielectric or mechanical properties, e.g. the electrical conductance or electric permittivity or density, of the material defining the internal structure of the object, specifically, by means of performing e.g. magnetic or electrical impedance/admittance or acoustic impedance measurements. To this end, at first the object under study is subjected to excitation through one or more points thereof, and then the response of the material of the object to the excitation is measured at one or more points of the object. The excitation and/or the response measurement can be performed at one or more frequencies and/or instants of time. The image of the object studied is created subsequently by an image reconstruction method on the basis of the thus obtained measurement data.

When further use (for e.g. inspection or diagnostics) of the image created by means of imaging is concerned, it is of critical importance that various errors getting incorporated into the measurement data during data acquisition be compensated to the greatest possible extent. The source of the measurement errors may be e.g. the measuring system used for the excitation and/or data acquisition, the individual excitation- and/or measuring units used in the measuring system, i.e. their systematic errors, or the errors arising from the geometric positions occupied by the excitation and/or measuring units during the measurement. Amongst these errors of soft-field tomographic systems, said systematic error is considered particularly important, because it cannot be measured by a preliminary calibration of the measuring system used for the analysis as due to the nonlinearity present in the system of the object and the measuring system, the object under study also influences the measuring system, and thus one or more parts thereof.

U.S. Publication Pamphlet No. 2010/0127705 A1 discloses a method and system for carrying out tomographic analysis based on magnetic induction. In order to perform the analysis, the object under study is subjected to an alternating magnetic field generated by excitation coils arranged around the object, then alternating current signals carrying information characteristic to the electrical conductance of the object and the spatial distribution of said conductance is captured by suitable receiving units arranged in positions surrounding the object. Data acquisition is carried out at least at two different frequencies. Using the thus recorded measurement data, particularly the imaginary parts thereof, a correction factor is derived through complicated mathematical algorithms, which may then be used for compensating the errors (scattered signals) arising due to a change in geometric positions of the excitation coils and/or receiving units. A drawback of the method is that only the imaginary part of the recorded data is used to derive the correction factor, which causes data loss. Furthermore, the method is also unable to manage systematic errors of the apparatus, the parts thereof, in particular, the excitation coils and/or receiving units.

U.S. Publication Pamphlet No. 2013/0013239 A1 discusses the use of phase modulated or phase- and amplitude modulated excitation generally in soft-field tomographic methods to enhance the resolution of data acquisition/imaging.

Figure 1:
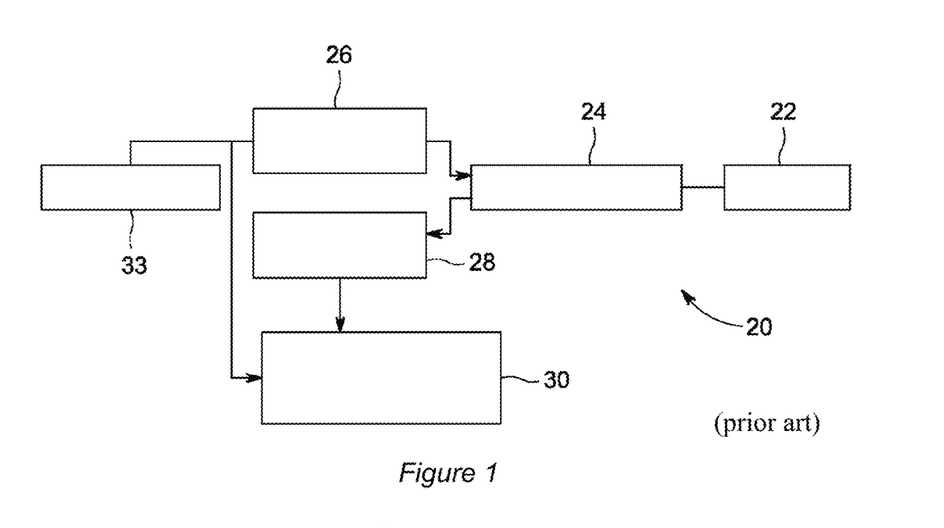
FIG. 1 is a block diagram of a prior art system for soft-field tomography data acquisition, which is not compensated for systematic and common phase errors, together common measurement error, caused by the data acquisition system.

U.S. Pat. No. 8,593,154 B2 discloses a method and apparatus to suppress artifacts arising in soft-field tomography investigation. The used data acquisition system 20 is shown in FIG. 1. Accordingly, the electrical properties of the material of the object 22 under study, in particular, its electrical conductivity and the spatial distribution of the electrical conductivity are analyzed by EIT method. To this end, a plurality of transducers are arranged on or near a surface of the object 22. The transducers are used firstly to excite the material of the object 22 in the desired manner (here, electrically) and secondly to capture the response of the material of the object to this excitation and convert it to electrical signals. Accordingly, the transducers are electrically connected firstly to the excitation units 26 providing their drive and secondly to the response detectors 28 for capturing signals representing the response. The signals of the response detectors 28 are passed on to a soft-field tomography module 30 connected to the response detectors 28, whose task is to calculate/evaluate the response of the object 22 to the excitation, and optionally solving the so-called inverse problem connecting the response, the excitation and the electrical conductivity-distribution in the object. The correct operation of the data acquisition system 20 is provided by the control unit 33, which is connected to the excitation units 26 and to the module 30. According to the disclosed solution, the object is subjected to excitation by the transducers 24 according to an excitation pattern comprising a plurality of frequency- and/or time component, then one or more artifacts of the imaging, particularly errors resulting from the geometric arrangement of the transducers and the inability of the electrodes used therein to be fitted to the forward predictive model used in the module 30 are desired to be eliminated by separating the response according to components. The excitation and data acquisition schemes described in detail however do not alleviate the systematic errors caused by the data acquisition system 20 and the subassemblies thereof, moreover these are not even mentioned.

In the soft-field tomography methods, thus particularly also in EIT and AIT measurements, the continuous (inhomogeneous, non-isotropic) medium (optionally comprising structural defects/deformations) is simplified to an impedance (or complex conductivity) network so that it may be managed with the toolset of numerical mathematics. To this end the material of the object under study is modeled with a linear network, whose mathematical description is solved and more or less well manageable;

the inverse problem is limited to calculating the impedance values on the branches of the network (generating the equation system is unequivocal, thus the inverse problem can be solved with greater safety);

the frequency-dependency of the material of the object under study may be estimated more accurately, because the impedances on each branch of the network may be modeled separately as a connection of electrical resistors, capacitors and inductors.

In the publication of H. Gagnon et al. entitled "*A Resistive Mesh Phantom for Assessing the Performance of EIT Systems*" published in 2009. in the magazine entitled IEEE Transactions on Biomedical Engineering in volume 57, Issue 9, pages 2257-2266, consideration regarding the design of a so-called phantom that can be used for the evaluation, comparison and calibration of EIT systems are discussed. The matrix method and the finite element method commonly used in solving electrical circuits is also discussed, and a method is also described for establishing a sufficiently accurate correspondence between the measurable parameters of the object under study and the impedance network modeling the object described by a directed network graph.

SUMMARY

Consequently, the object of the present invention is to provide a data acquisition/processing method and measuring system primarily for soft-field tomographic material analysis/imaging method, which is suitable for taking into account the systematic and common phase errors of the units used to carry out the soft-field tomography methods, in particular, the excitation units and also suppressing thereof in the recorded measurement data. As a result of the elimination of said systematic errors from the measurement data, the accuracy of data serving as the basis of the imaging is improved, which allows more accurate imaging of the of the internal structure of the object under study.

A further object of the present invention is providing a data acquisition/processing method and measuring system primarily for soft-field tomography material analysis/imaging method, which is more reliable than other similar methods used nowadays regarding the solution of the equation system obtained in the linear network model approximation, i.e. regarding the determination of the unknown impedance values corresponding to the material properties of the analyzed object, i.e. actually regarding the solution of the inverse problem. The more reliable solution of the inverse problem also facilitates the improvement of the accuracy and resolution of the soft-field tomography imaging.

A further object of the invention is to generally improve soft-field tomography imaging methods by providing a data acquisition/processing method and measuring system, which provides an improved data acquisition protocol to derive the equation system required for the solution of the inverse problem.

In our studies we have come to the conclusion that systematic and common phase measurement errors of the subassemblies of the data acquisition measuring system (including the cables used for electrical connections) will occur as a single common measurement error affecting each piece of the measurement data, and thus its suppression and compensation is simplified if the measuring units that are parts of the data acquisition measuring system and the excitation units providing the excitation of the object under study, i.e. the signal generator used in the measuring system is connected to a common potential, e.g. to the ground potential, and measurement of the response of the object to the excitation relative to the ground of the signal generator, i.e. the data acquisition with the measuring units is also carried out relative to the ground of the signal generator. Particularly, if preferably a single reference element with a known purely ohmic resistance is inserted into the measuring circuit at the side of the signal generator on said common potential, the measurable phase shift occurring on the reference element is the result of the common measurement error, thus its extent may be simply determined by a phase shift measurement carried out on the reference element, and the measurement data can be compensated with its known value.

In our studies we have come to the further conclusion that to solve the inverse problem, it is preferable to carry out the data acquisition so as to ensure that the number of equations required to determine the impedance/admittance values belonging to the branches of the corresponding directed network graph at a certain level of discretization of the material of the object studied, i.e. at a given resolution of the data acquisition, surely exceed the number of unknowns in said equations. To put it differently, the data acquisition is preferably carried out so as to ensure that the derived equation system for solving the inverse problem is overdetermined. In our studies we have found that a data acquisition performed in line with this requisite can also be ensured with the application of relatively simple excitation schemes if the excitation of the object under study is carried out in a given excitation/response detection configuration at more than one frequencies simultaneously or one after the other. Details of such a data acquisition is described in detail in what follows in relation to the exemplary embodiment.

BRIEF DESCRIPTION OF THE DRAWINGS

In what follows, the invention is described in detail with reference to the accompanying drawings, wherein.

DETAILED DESCRIPTION

The data acquisition/processing method and system according to the invention to be used in connection with soft-field tomographic analysis/imaging methods is described in detail in the following in relation with such an embodiment thereof, which is related to the EIT method. Accordingly the data acquisition/processing method and system is described in connection with electric excitation and measurement of response thereto. Accordingly the object to be subjected to soft-field tomography analysis is subjected to electric excitation in this embodiment of the invention and the response obtained as a result of the electric excitation is considered the basis (input) of the solution of the system of equations established in the linear network model approximation (directed graph). However, it is obvious to a person skilled in the art, that embodiment of the data acquisition method that is described in detail in the following may also be used in relation with different types of soft-field tomography methods after the suitable modification of the type of used excitation/response measurement.

According to a preferable exemplary embodiment of the solution according to the invention, the object under study is modeled with an impedance network, so the mathematical representation of the model is a directed (weighted) graph. The structure of the graph representing the object under study follows the same principles at any resolution of the soft-field tomography data acquisition. Given the number of measuring elements (el=1, 2, 3 . . . ; positive integer) desired to be used for measuring the analyzed object e.g. by placement on its surface or near its surface, and the desired number of shells (sh=0, 1, 2, 3 . . . ; positive integer) to form the graph, which information is practically equivalent to the desired resolution of studying of the object under study or the internal structure thereof, the geometric parameters unequivocally characterizing the graph (i.e. the linear network), i.e. the number of nodes (n), branches (br) and closed loops (l) of the graph can be calculated by the following expressions number of nodes: $n = el \times (sh+1) + 1$;

number of branches: $br = el \times (3 \times sh + 2)$; and number of loops: $l = el \times (2 \times sh + 1)$.

Figure 2A:
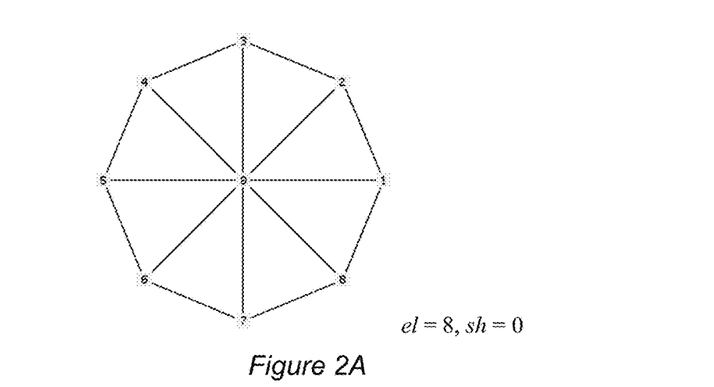
FIGS. 2A and 2B show a few simple examples of directed graphs corresponding to discretization forming the base of the soft-field tomography data acquisition method according to the invention.
Figure 2B:
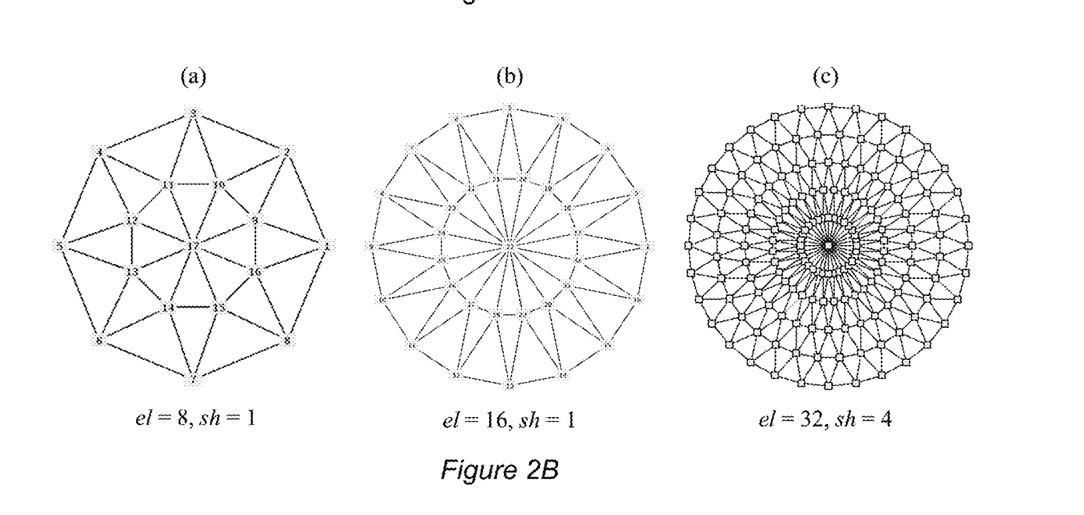

A few such exemplary graphs obtained by the discretization and linear network model approximation of the object under study are illustrated in FIGS. 2A and 2B, where FIG. 2A shows a graph corresponding to the choice of el=8, sh=0 and FIG. 2B (see graphs marked (a), (b) and (c)) illustrates cases with higher resolution (more shells) and/or more measuring elements; it is obvious that the number of measuring elements and/or the number of shells may be chosen arbitrarily.

When the object under study is discretized, the position coordinates of the nodes of the graph are chosen according to the optimal solution of the actual analysis task. The impedance (or admittance) values representing each branch have to be calculated for the soft-field tomographic characterization (imaging).

It is generally typical for the thus obtained graphs, that the nodes on the extremities (outer perimeter) of the graph represent the measuring elements. The physical basis of this is that the field properties are to be determined by measurement or e.g. calculated in these points.

It is hereby noted that—as it is known to a person skilled in the art—the graph obtained according to the aforementioned may be described for quantitative characterization in matrix representation, generally by a so-called node-branch matrix (a size of which is br×n) and a so-called loop-branch matrix (a size of which is br×l), which matrices comprise elements with values of −1, 0 or 1 depending on the relative positions of nodes, branches and loops.

When using soft-field tomography analysis methods, the solution of the inverse problem, i.e. the image reconstruction requires the solution of a nonlinear system of equations. In order to determine the impedance values represented by the branches of the directed graph representing the object, the measurement data acquired by the measuring elements on the perimeter of the graph (i.e. the measured data of the response of the object to the excitation) is substituted into the system of equations concerning the network corresponding to the graph. Description of the derivation of the system of equations and the necessary mathematical tools can be found e.g. in the U.S. Publication Pamphlet No. US 2011/0163770 A1, and thus these are not described in detail herein. A basic requisite of the solvability of the system of equations is that it should not be underdetermined. Keeping that in sight, the data acquisition scheme to be described in detail in the following is selected so that the system of equations is overdetermined for the conductivity and capacity values on each branch of the graph.

As graphs are used for modeling the object under study, the properties of the system of equations to be solved may be described by the following expressions:

number of equations: $eq = g \times (n-1) = g \times el \times (sh+1)$; and number of unknowns: $x = 2 \times br + g \times (eq - el)$, where n is the number of the nodes of the graph, br is the number of the branches, el is the fixed number of measuring elements and sh is the number of shells characterizing the fineness of the resolution (also including the generator pole shifts g).

The system of equations can be made overdetermined by the number of generator positions. The optimal value of g can be determined with the expression g=6×(sh+1).

It is hereby noted that a change in the number of measuring elements does not affect the solvability of the mathematical problem, because the value of g is independent of the number of measuring elements el. This means practically that the resolution of the soft-field tomography imaging can be increased without deteriorating the solvability of the inverse problem. Realization of the measuring method is always determined by the desired resolution (image detail).

The properties of the system of equations obtainable by the data acquisition with the aforementioned parameters is summarized in the following Tables 1 and 2 with increasing the resolution, i.e. with the choice of values of sh=1 and sh=5 respectively. It can be seen from the tables that the number of equations indeed exceed the number of unknowns independently of the number of measuring elements.

TABLE 1

| sh = 1. | | | | | |
|---|---|---|---|---|---|
| el | sh | n | br | g | eq | x |
| 8 | 1 | 17 | 40 | 12 | 192 | 176 |
| 16 | 1 | 33 | 80 | 12 | 384 | 352 |
| 32 | 1 | 65 | 160 | 12 | 768 | 704 |
| 64 | 1 | 129 | 320 | 12 | 1536 | 1408 |

TABLE 2

| sh = 5. | | | | | |
|---|---|---|---|---|---|
| el | sh | n | br | g | eq | x |
| 8 | 5 | 49 | 136 | 36 | 1728 | 1712 |
| 16 | 5 | 97 | 272 | 36 | 3456 | 3424 |
| 32 | 5 | 193 | 544 | 36 | 6912 | 6848 |
| 64 | 5 | 385 | 1088 | 36 | 13824 | 13696 |

Generally speaking, when the data acquisition is carried out in accordance to the aforementioned, el number of measuring elements (in the case of EIT measurement, preferably metal electrodes) are available on or near the surface of the object under study arranged according to an arbitrary geometry, which are connected in pairs to form a measuring circuits for each measurement, i.e. for obtaining each piece of measurement data and a measuring unit is included in each measuring circuit. The number of possible combinations is $el^2$, which is equal to the maximal number of measurements. This way each possible combination has an equation system corresponding thereto. As the same object is measured during the excitations carried out one after the other, the unknown variable of each acquired equation system is the same impedance matrix. Accordingly the data acquisition scheme results in an overdetermined equation system.

Before establishing a system of equations, the object is subjected to excitation at a certain frequency through the measuring elements. If the grounded connector, from now on the ground point or cold spot (0 V; GND) of the signal generator carrying out the excitation is connected to one of the measuring elements, the other connector, representing—from now on—the alive point or hot spot (+I; GEN) of the signal generator, can be connected to any one of the remaining n−1 measuring elements. After completion, a measurement is carried out by the measuring circuits at this temporally fixed connector position of the signal generator, then the hot spot +I of the signal generator can be relocated to another measuring element. If the cold spot GND of the signal generator is relocated to another measuring element, again n−1 possibilities become available for relocating said hot spot +I of the signal generator; that is, by exploiting the reconnection possibilities discussed here, a maximum of $el^2$ measurements can be performed.

In order to actually carry out the measurements, one connector of the measuring unit of each measuring circuit is connected to the measuring element, and the other connector of the measuring units is connected to the cold spot GND of the signal generator. This way the potential of each measuring element is measured by the measuring units of the measuring circuits during the data acquisition.

Figure 4:
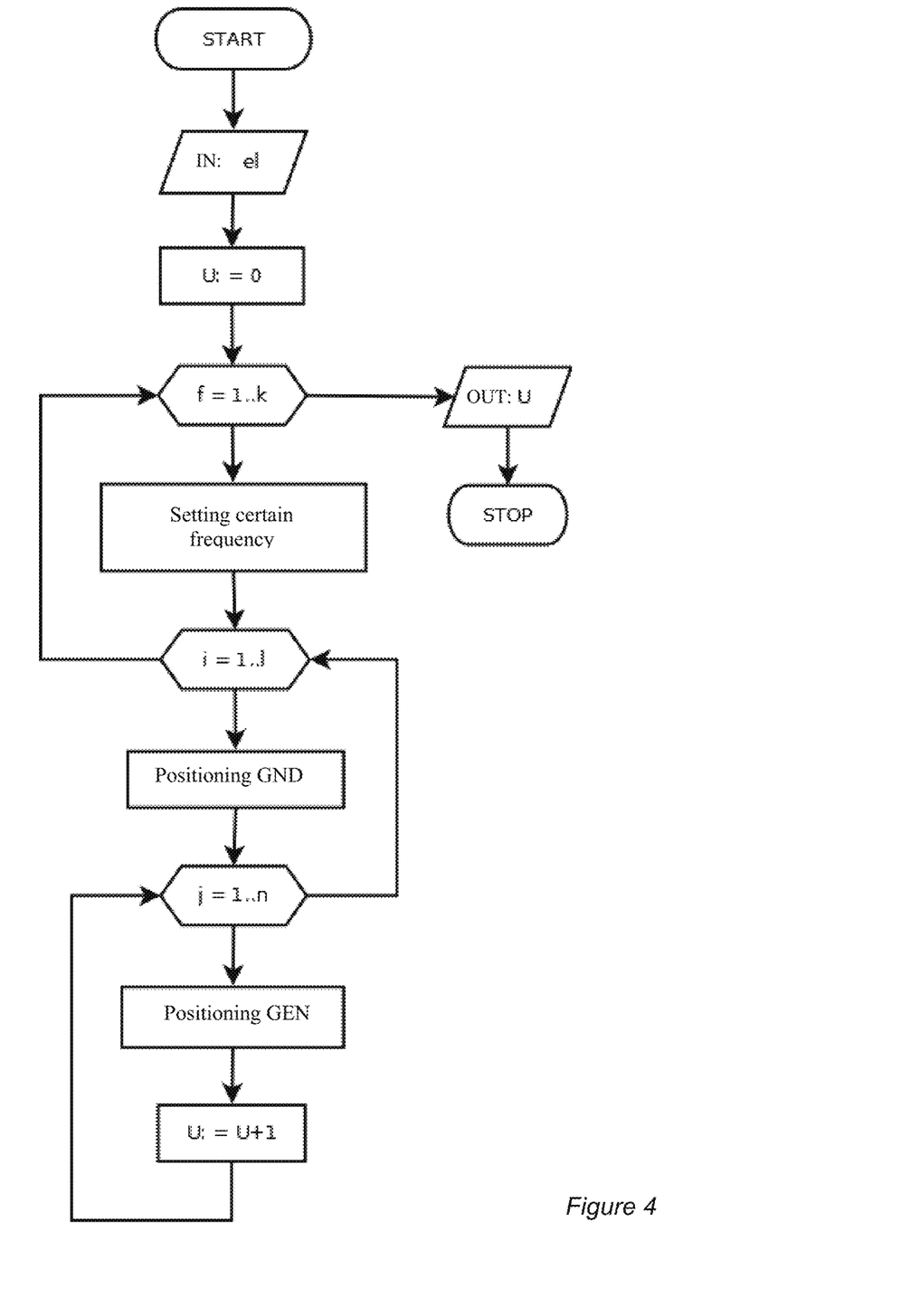
FIG. 4 shows an exemplary implementation of the systematical execution of the excitation carried out by the signal generator during the data acquisition in the form of a flow-chart.

Systematic scanning performed through each measuring element by the hot and cold spots of the signal generator in accordance with the aforementioned can be tracked on the flow chart of FIG. 4. Obviously, during the data acquisition only the hot- and cold spot (GEN; GND) of the signal generator is "moved" from measuring element to measuring element (i; j), while measurements are carried out on each of the measuring circuits formed by the pairs of the measuring elements and the results (U) thereof are recorded, optionally modifying the excitation frequency (f) between each measurement.

According to our experiences, it is advantageous regarding the data processing to carry out measurements in each signal generator connector arrangement also with reversed phase, because the measurement results obtained when repeating a system of equations also take part in the solution and thus increase the measurement accuracy.

An advantage of the method is that the connectors of the measuring units connected to a common ground do not need to be lead out of the measuring element, thus only the remaining points are lead out. This reduces the frequency-dependent error caused by scattered capacitances and the measurement is simplified. If necessary, differences of each point may be generated digitally.

The scheme of the data acquisition used by us comprises the following main steps: (i) each (el pieces of) measuring elements are galvanically connected to one of the differential measuring inputs of a measuring unit, while the other differential measuring input of each measuring unit is fixedly connected to the cold spot (i.e. the grounding) of the signal generator providing the excitation signal (the positions of the measuring inputs do not change during measurements);

(ii) the cold spot (0 V; GND) of the signal generator is connected to a first measuring element;

(iii) the hot spot (+I; GEN) of the signal generator is connected to a second measuring element located in the same measuring circuit as the first measuring element;

(iv) the object is subjected to excitation generated by the signal generator on a certain (first) frequency through the first and the second measuring elements;

(v) simultaneously carrying out the measurement of the response of the object to the excitation on every measuring circuit for generating equation system;

(vi) the overdetermined equation system is produced by repeating steps (ii) to (v), where the excitation of the object in step (iv) is optionally carried out on one or more frequencies different from the certain (first) frequency.

Figure 3A:
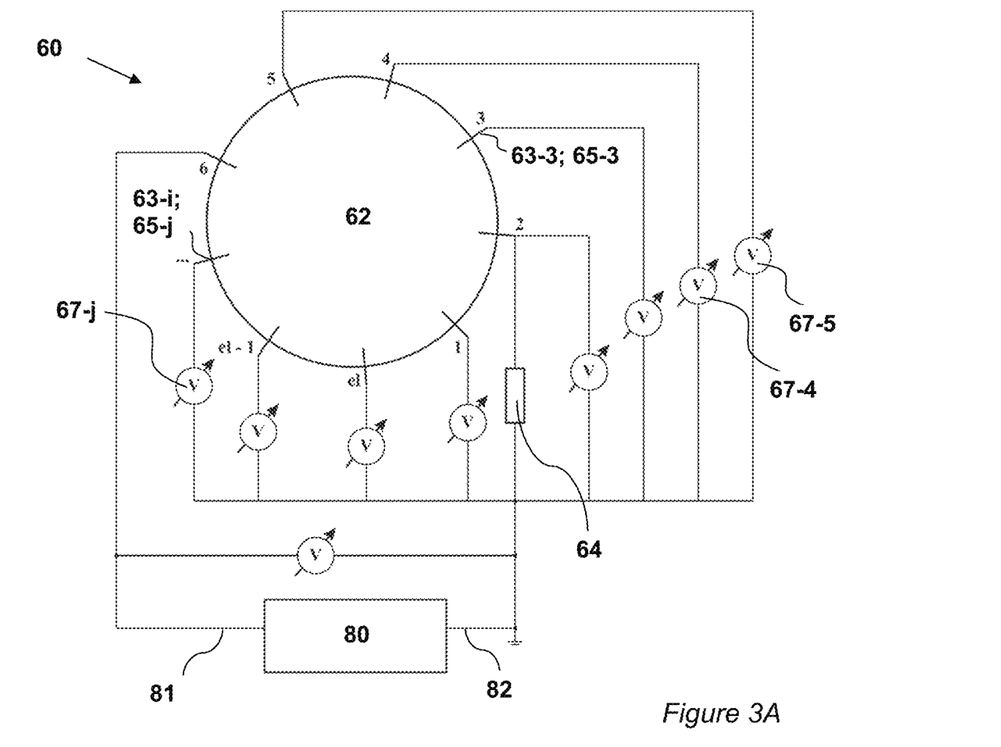
FIG. 3A is a block diagram of the measurement system according to the invention suitable for soft-field tomography data acquisition and compensated for common measurement error.
Figure 3B:
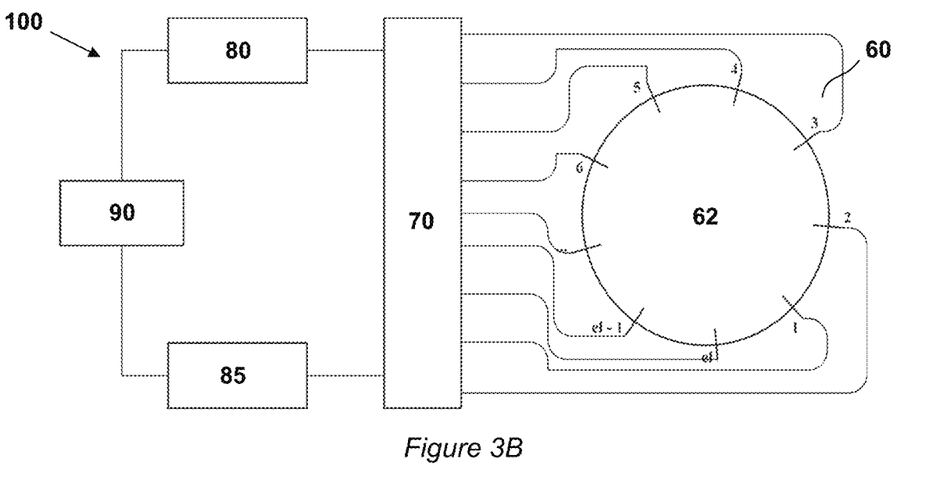
FIG. 3B illustrates an exemplary connection diagram of the soft-field tomography data acquisition system according to FIG. 3A with using a given number of transmitting units/receiving units (transducers)

In conformity with FIGS. 3A and 3B, the general data acquisition scheme described above is carried out in a preferable implementation by the data acquisition system 60 according to the following: transmitting units 63-1, 63-2, . . . , 63-el' (from now on 63-i; i=1, 2, . . . , el') are arranged on the surface of the object 62 under study in a substantially arbitrarily selected geometric arrangement. The transmitting units 63-i are connected to the connectors of the signal generator 80 by suitable conduits, preferably through a multiplexer 70. The signal generator 80 is connected to a control device 90; in response to a suitable control signal of the control device 90, the signal generator emits an excitation signal having a predetermined signal shape, which is introduced into the object 62 by any two (i.e. one pair) of the transmitting units 63-i selected by the multiplexer 70 (according to FIG. 3B in this example, by the transmitting units marked no. 2 and 6). Thus an excitation field is generated in the object 62. The introduction is particularly carried out so that the hot spot 81 of the generator 80 is connected to one of the selected transmitting units (in the example according to FIG. 3B to the transmitting unit no. 6), while the cold spot 82 (i.e. grounding) of the signal generator 80 is noccented to the other one of the selected transmitting units (in the example according to FIG. 3B to the transmitting unit no. 2).

During data acquisition, the response of the object 62 to the excitation is measured/recorded. In order to carry out the measurement, receiving units 65-1, 65-2, . . . , 65-el (from now on: 65-j; j=1, 2, . . . , el) or measuring units are placed on the surface of the object 62 under study in a substantially arbitrarily selected geometric arrangement. The receiving units 65-j are arranged so that they have a common ground that is the same as the cold spot 82 of the signal generator 80. In order to carry out the measurement, the receiving units 65-j form measuring circuits/measuring channels having common grounds in substantially arbitrary pairing through the multiplexer 70. The actual pairing to be used in a given measurement (measurement configuration) is provided/carried out by the multiplexer 70 according to a fix algorithm (see e.g. FIG. 4). At least one measuring unit 67-1, 67-2, . . . , 67-el (from now on: 67-j; j=1, 2, . . . , el) corresponds to each thus obtained measuring circuit. The receiving units 65-j detect the response (qualitative characterization) in different geometric positions on the object 62 given to the excitation field generated in the material of the object 62 by the transmitting units 63-i, while the measuring units 67-j provide the expression of the response with numerical values (measurement data) i.e. the quantitative characterization. The measurement data obtained in the actual measuring configuration are transferred through the multiplexer 70 to the measuring data acquisition unit 85, which is connected to the control unit 90 in a suitable manner. In order to facilitate the simple measurement of the systematic and common phase errors (from e.g. the connecting conduits) caused by the whole of the data acquisition system, a reference element 64 (preferably being well measurable with known parameters, thus with a given ohmic resistance) is inserted between the cold spot 82 of the signal generator 80 and one of the receiving units of one of the measuring circuits used for data acquisition in the actual measuring configuration into this measuring circuit.

According to the data acquisition method, independent of the geometric position of the connectors of the signal generator 80 (i.e. of the hot 81 and cold 82 spots) measurement is carried out simultaneously/at the same time on each receiving unit 65-j relative to the cold spot 82 of the signal generator 80. The positions of the differential measuring inputs of the measuring circuits are not changed during the data acquisition at any given measurement configuration, only the connectors of the signal generator 80 are placed—independently of each other—to different geometric positions on the object 62 by the multiplexer 70 preferably during a systematical scanning.

Accordingly, the grounds of the signal generator 80 and the receiving units 65-j are common. Thus the excitation and the data acquisition (measurement) are carried out relative to the common point. Although the excitation and the measurement is carried out relative to the common point, the common point in said method does not correspond to 0 V, but to a value offset from that by a constant. The offset is caused by the reference element 64 (preferably a purely ohmic resistor) with known resistance inserted on the cold spot 82 side of the signal generator 80. The common measurement errors (effectively the systematic error of the signal generator 80, common phase errors etc.) occurring when measuring the object 62 under study also occur on the reference element 64. As the resistance of the reference element 64 is known, the potential values measured on the object 62 by the measuring units 67-j in each measuring circuit can be simply compensated, i.e. the measurement data that could be obtained by a measurements relative to 0 V can be simply generated therefrom e.g. by subtraction. As a result of including the reference element 64, the systematic errors are greatly reduced during processing of the measurement data (e.g. by subtraction, ratio calculation), i.e. by carrying out the data acquisition with the inserted reference element 64, the measurement data can be practically made independent of the common measurement errors of the data acquisition system 60 that were thought to be impossible to be eliminated in the past. A further advantage of the method is that it also reduces statistical errors. This is important firstly because soft-field tomography imaging methods require measurement data relative to 0 V, secondly soft-field tomography imaging methods are exceptionally sensitive for uncompensated errors occurring in the measurement system and during measuring processes, therefore improvement of the quality of the imaging requisites the reduction of errors.

The transmitting units 63-i and/or the receiving units 65-j may be arranged directly on the surface of the object 62 under study, e.g. in the form of metal electrodes. It is hereby noted, that the transmitting units 63-i and/or the receiving units 65-j may also be arranged inside (i.e. penetrating into) the object 62 for excitation and/or for data acquisition. E.g. needle electrodes may serve as an example of such an arrangement.

Moreover a transmitting unit 63-i and a receiving unit 65-j may also be formed as a single integrated measuring sensor, or with other words as a transducer, which significantly simplifies the creation of the measuring system. In such a case, the measuring system 100 preferably comprises transmitting units and receiving units in identical number, i.e. el'=el is satisfied, but this is not necessary.

Furthermore it is obvious, that generally different types of excitation may be generated in the material forming the object 62 by the transmitting units 63-i based on the type thereof, among others e.g. electric, magnetic, optical or thermal excitation. Based on the type of the excitation, the coupling of the transmitting units 63-i, the receiving units 65-j, or transducers, and the object 62 may be of different nature, e.g. electric, capacitive, galvanic, heat-exchanging and so on.

The excitation waveform is generally a (pure) sinusoidal/cosinusoidal waveform, but the excitation itself may be carried out by a bipolar square signal provided by the signal generator 80. Moreover, the signal generator 80 may also be operated in current generator or voltage generator operation mode.

As it is obvious in the light of the aforementioned, in a preferable embodiment of the measuring system 100 suitable for soft-field tomography data acquisition illustrated schematically in FIG. 3B comprises the data acquisition system 60, the signal generator 80 and measuring data acquisition unit 85 connected thereto through the multiplexer 70, and the control unit 90 for controlling the signal generator 80 and the measuring data acquisition unit 85 and optionally for carrying out the (pre)processing of the measured data, together with any necessary accessories—known to a person skilled in the art—e.g. suitable signal amplifiers, signal conditioning units, optionally with further noise-filters and other similar devices (e.g. power supply, conduits etc.) necessary for the operation of the measuring system 100. The multiplexer 70 is a suitably programmable unit to provide excitation in different, systematically selected and scanned transmitting unit positions. Similarly to provide the systematical execution of data acquisition, the measuring data acquisition unit 85 itself is also configured as a programmable unit. Furthermore, for the simple storage and optional processing of measurement data, the control device 90 may be provided in the form of a personal computer (PC) or a programmable microcontroller. Implementing the control device 90 as a personal computer is particularly preferable, if soft-field tomography imaging is also to be carried out based on the measured data.

It is also noted, that in the case of e.g. electric excitation, the measuring units 67-j may also be provided in the form of ordinary voltmeters, however in cases where the number of measuring units 67-j is relatively high, they are preferably provided in the form of high-resolution precision measuring devices (e.g. lock-in amplifiers). It is particularly preferable to use devices based on the lock-in principle in cases where the data acquisition is carried out on e.g. a plurality of frequencies.

The measurement data obtained by the data acquisition according to the aforementioned:
- are potential values (because they are effectively measured relative to 0 V);

$$\left[0, -20 \cdot lg \frac{U_2^3}{U_I^3}, 0, -20 \cdot lg \frac{U_4^3}{U_I^3}, -20 \cdot lg \frac{U_5^3}{U_I^3}, -20 \cdot lg \frac{U_6^3}{U_I^3}, -20 \cdot lg \frac{U_7^3}{U_I^3}, -20 \cdot lg \frac{U_8^3}{U_I^3}\right]^T == [0, A_2^3, 0, A_4^3, A_5^3, A_6^3, A_7^3, A_8^3]^T$$

- do not contain the (frequency-dependent, temporally constant) common phase error; and
- are free of error-superimposition.

Said raw measurement data is subjected to preprocessing before being used in soft-field tomography imaging, preferably by the control device itself; however the preprocessing may also be carried out by a dedicated processing unit. The goal of the preprocessing is the linearization of the data to be imported into the soft-field tomography imaging algorithm e.g. for the (in this case impedance-based) reconstruction of the internal structure of the object under study, and to detach it from the data acquisition system used for acquiring measurement data, and from common measurement errors.

To this end, in a first step, the raw data is arranged in a vector having n elements, in the following form:

$$\underline{u}_n^i [u_1^i, u_2^i, u_3^i, \ldots, u_{n-1}^i, u_n^i]^T,$$

where $u_n^i$ is the potential value measured in the n-th node of the directed graph in the i-th excitation configuration.

During the data acquisition, a maximum number of $el^2$ of such vectors may be recorded. Two potential values with distinguished roles are selected in each such vector:
- $u_0^i$ is the potential value measured at the position of the cold spot (GND) of the signal generator, and
- $u_I^i$ is the potential value measured on the hot spot +I (GEN) of the signal generator.

In a specific example, e.g. with n=8, if the cold spot GND of the signal generator is on the 3rd measuring element during the scanning and its hot spot +I is on the first measuring element, in the measuring configuration number 3 (i.e. i=3) (see FIG. 3A), then the vector comprising the potential values is in the following form:

$$\underline{u}_8^3 [u_I^3, u_2^3, u_0^3, u_4^3, u_5^3, u_6^3, u_7^3, u_8^3]^T.$$

The preprocessing of the raw measurement data is further demonstrated in this specific example. During preprocessing:

(1) The value of $u_0^i$ is subtracted from each piece of measurement data (suppression of common phase error), which yields the following result according to the example:

$$[u_I^3 - u_0^3, u_2^3 - u_0^3, 0, u_4^3 - u_0^3, u_5^3 - u_0^3, u_6^3 - u_0^3, u_7^3 - u_0^3, u_8^3 - u_0^3]^T.$$

(2) As the pieces of measurement data are complex quantities (as a result of the sinusoidal/cosinusoidal excitation), each of them are notated in exponential form, thus the amplitude- and phase vectors of $$[U_1^3, U_2^3, 0, U_4^3, U_5^3, U_6^3, U_7^3, U_8^3]^T \text{ and } [\varphi_1^3, \varphi_2^3, 0, \varphi_4^3, \varphi_5^3, \varphi_6^3, \varphi_7^3, \varphi_8^3]^T$$

respectively are obtained according to the example.

(3) Using the formula of $$A_i = -20 lg \frac{U_i^3}{U_I^3},$$

attenuation values are calculated from each element of the amplitude vector:

(4) Using the formula of $$Z_I^i = R \cdot \frac{U_I^i}{U_0^i},$$

the summated impedance value of $Z_I^i$ between the cold spot and hot spot of the signal generator is calculated from the value of $U_0^i$; where $U_0^i = |u_0^i|$ and R is the resistance of the reference element 64 inserted on the cold side of the signal generator (see FIG. 3A). According to the example, the $$\left[R \cdot \frac{U_1^3}{U_0^3}, -20 \cdot lg\frac{U_2^3}{U_I^3}, 0, -20 \cdot lg\frac{U_4^3}{U_I^3}, -20 \cdot lg\frac{U_5^3}{U_I^3}, -20 \cdot lg\frac{U_6^3}{U_I^3}, -20 \cdot lg\frac{U_7^3}{U_I^3}, -20 \cdot lg\frac{U_8^3}{U_I^3}\right]^T == [Z_I^3, A_2^3, 0, A_4^3, A_5^3, A_6^3, A_7^3, A_8^3]^T$$

vector can be obtained.

(5) After this, the value of $\varphi_I^3$ is subtracted from all non-zero elements of the phase vector, thus obtaining the $$[0, \varphi_2^3 - \varphi_I^3, 0, \varphi_4^3 - \varphi_I^3, \varphi_5^3 - \varphi_I^3, \varphi_6^3 - \varphi_I^3, \varphi_7^3 - \varphi_I^3, \varphi_8^3 - \varphi_I^3]^T = [0, \overline{\varphi}_2^3, 0, \overline{\varphi}_4^3, \overline{\varphi}_5^3, \overline{\varphi}_6^3, \overline{\varphi}_7^3, \overline{\varphi}_8^3]^T$$

phase vector.

(6) The phase angle of the summated impedance measurable between the cold spot and hot spot is obtained by the $\varphi_Z^i = \varphi_I^i - \varphi_0^i$ formula, where $\varphi_0^i = \mathrm{arc}(u_0^i)$ is the phase of the voltage measured at the cold spot of the signal generator, i.e. on the reference element 64. Accordingly, in the example:

$$[\varphi_I^3 - \varphi_0^3, \varphi_2^3 - \varphi_I^3, 0, \varphi_4^3 - \varphi_I^3, \varphi_5^3 - \varphi_I^3, \varphi_6^3 - \varphi_I^3, \varphi_7^3 - \varphi_I^3, \varphi_8^3 - \varphi_I^3]^T$$

$$[\varphi_Z^3, \overline{\varphi}_2^3, 0, \overline{\varphi}_4^3, \overline{\varphi}_5^3, \overline{\varphi}_6^3, \overline{\varphi}_7^3, \overline{\varphi}_8^3]^T.$$

As a result of the transformations carried out in steps (1) to (6), the data vectors acquired in the i-th measuring configuration according to the example and also compensated regarding the systematic error caused by the data acquisition system are obtained in the form:

$$[Z_I^3, A_2^3, 0, A_4^3, A_5^3, A_6^3, A_7^3, A_8^3]^T \text{ and } [\varphi_Z^3, \overline{\varphi}_2^3, 0, \overline{\varphi}_4^3, \overline{\varphi}_5^3, \overline{\varphi}_6^3, \overline{\varphi}_7^3, \overline{\varphi}_8^3]^T.$$

That is to say the raw measurement data is converted into the form of attenuation- and phase data as a n×i sized matrix that can be used in the image reconstruction of soft-field tomography analysis methods, particularly of an EIT method by the transformations carried out according to the above steps of (1) to (6).

The advantage of said preprocessing is that
  it increases the suppression of the common phase error (due to the high resolution, frequency-dependent subtraction of the measurement results);
  it reduces the nonlinear errors of the amplitude as a result of the ratio calculation;
  it suppresses the systematic errors (the phase error of the signal generator) of the system (in particular of the signal generator);
  it detaches the measurement results from the conditions of the data acquisition, and from the measuring system (it fixes the transfer properties of the object under study).

One of the advantages of the used impedance model is that the impedance (or admittance) values on each branch are frequency-dependent. This means, that the measurement results of measurements carried out on different frequencies are different, but the parameters (resistance, capacity etc.) used for their processing are the same in every equation system. This provides opportunity to double the number of equations by repeating the data acquisition scheme described above on a different frequency. Therefore it is not necessary to run the data acquisition for el² number of possibilities, as number of equation systems may be multiplied by carrying out the excitation on a second, a third, etc. frequencies. As a result, the equation system to be solved can be made overdetermined for graphs of any complexity. Accordingly, when the soft-field tomography analysis is planned, the goal is to find frequencies preferably optimal for the measurement. The raw measurement data obtained on different frequencies are stored in two n×i sized matrices per frequencies during the aforementioned preprocessing.

Summary: according to the aforementioned, the object of the invention is a data acquisition/processing method and measuring system for mapping the selected properties of an object under study, to be used as part of a soft-field tomographic (nondestructive) material testing method (imaging). During data acquisition, preferably the parameters of an electric field generated in the material of the object are determined, preferably on at least one frequency, by measuring units preferably arranged on the surface of the object under study and connected to the same potential as the signal generator, preferably on its cold side which is on ground potential. After this, the internal (i.e. volumetric) structure of the analyzed object may be determined by establishing and solving the equation system according to the linear network model approximation corresponding to the measurement data. By introducing a reference element formed by a resistance of known value to the cold side of the signal generator in the measuring system used for carrying out the soft-field tomography measurements, the systematic error caused by the entire data acquisition system and the common phase error of the data acquisition system can be determined, and the obtained raw measurement data may be compensated for this so-called common measurement errors. The object under study is preferably modeled by an (electric) impedance network characterized by a directed network graph for carrying out the calculations. By carrying out the data acquisition in a plurality of geometric points and on a plurality of frequencies, better resolution may be achieved than before, and the information content of the measurement data is also significantly increased.

Obviously, multiple types of data acquisition may be carried out together/in combination by suitable selection of the transmitting units/receiving units for each data acquisition positions. This also increases the resolution of the soft-field tomography analysis method, and significantly increases the information content of the measurement data.

It is also noted, that in order to simplify the complicated internal structure of the object under study and the complicated electric field generated in the material of the object, and—if necessary—to take into account the electric field generated outside the object under study which acts back on the object, the linear network associated with the object under study can be transformed into a more simple geometric form by e.g. Mobius transformation, thus the analysis of the created potential field becomes more simple. As a result of the transformation, discretization of the material of the object under study follows the electric field created therein more closely, thus the impedance values obtained by the solution of the inverse problem characterize the internal structure of the object under study more accurately, which results in the improvement of the soft-field tomography imaging/analysis.

The invention claimed is:

1. Measuring system for data acquisition in soft-field tomography analysis of an object, the measuring system comprises transmitting units, receiving units, measuring units, an excitation unit having an alive point and a ground point ("cold spot"), a measuring data acquisition unit and a control unit, wherein in an operational state of said measuring system the control unit is operatively connected to the excitation unit and the measuring data acquisition unit to control the excitation unit and the measuring data acquisition unit;

the excitation unit is simultaneously connected through its hot spot and cold spot to a transmitting unit, one at a time, to drive the transmitting units, wherein the cold spot of the excitation unit corresponds to power ground;

at least the transmitting units connected to the excitation unit are coupled, one by one, with the object under study to create an excitation field within the object;

the receiving units are coupled, one by one, with the object under study to detect response upon the excitation field within the object, wherein the receiving units are connected together in pairs to form measuring circuits to characterize the response detected by said receiving units quantitatively by measurement data, wherein individual ones of the measuring circuits comprise a measuring unit—with at least a first measuring input and a second measuring input for said quantitative characterization, said first and second receiving units of the measuring circuits are connected to the first and second measuring inputs, respectively, of the measuring unit in said measuring circuit, and power ground of each of the receiving units is connected to the cold spot of said excitation unit; and the measuring units of each measuring circuit are connected to the measuring data acquisition unit to acquire the measurement data; and a reference element is inserted into one of the measuring circuits into between the cold spot of the excitation unit and one of the receiving units connected to the cold spot to shift the respective measurement data provided by said respective receiving unit connected to the cold spot by an offset value.

2. The measuring system according to claim 1, further comprising a multiplexer, said multiplexer inserted into between the excitation unit and the transmitting units driven by the excitation unit, as well as each of the receiving unit and the measuring data acquisition unit, said multiplexer is configured to operatively connect the transmitting units connected to the excitation unit with the receiving units forming each measuring circuit into arbitrary pairs.

3. The measuring system according to claim 1, wherein the reference element is provided by an element of known parameters, and the offset value is a constant value.

4. The measuring system according to claim 1, wherein the measuring inputs of the measuring units are differential measuring inputs.

5. The measuring system according to claim 1, wherein the measuring units comprise precision measurement devices with high resolution.

6. The measuring system according to claim 1, wherein the excitation unit comprises a signal generator capable of operating as either a current generator or a voltage generator in its operational state.

7. The measuring system according to claim 1, wherein the transmitting units comprise devices configured to electrical excitation of the object under study, and the measuring units comprise voltmeters.

8. The measuring system according to claim 1, wherein the transmitting units and the receiving units are configured as devices suitable for being arranged on a surface of the object under study.

9. The measuring system according to claim 1, wherein the transmitting units and the receiving units are configured as devices suitable for being disposed at least partially within a volume of the object under study.

10. The measuring system according to claim 1, wherein the transmitting units and the receiving units are selected from a group comprised of metal electrodes and pin electrodes.

11. The measuring system according to claim 1, wherein a coupling between each of said transmitting units and/or receiving units and the object under study is selected from a group comprised of electric, capacitive, galvanic, heat exchanging and optical couplings.

12. The measuring system according to claim 1, wherein the transmitting units and the receiving units comprise measuring detectors comprising integrally functions of both the transmitting units and the receiving units.

13. The measuring system according to claim 1, wherein the object is provided by an object with inhomogeneous material distribution.

14. Method for data acquisition in soft-field tomography analysis of an object, the method comprising:
(i) bringing transmitting units and receiving units into coupling with the object in arrangements with certain geometric patterns;
(ii) subjecting the object to volumetric excitation by at least one pair of the transmitting units through driving said pair of transmitting units by an excitation signal generated by an excitation unit, connecting one transmitting unit of the transmitting units forming said pair(s) to the hot spot of the excitation unit and connecting the other transmitting unit to the cold spot of the excitation unit, wherein the cold spot of the excitation unit corresponds to power ground;
(iii) creating measurement data by measuring complete response of the object to the excitation by the measuring circuits created from receiving unit pairs formed by the receiving units, wherein each measuring circuit further comprises at least one measuring unit, the measuring unit having a first measuring input and a second measuring input, wherein—when carrying out the measurement—one receiving unit of each receiving unit pair coupled with the object is connected to the first measurement input and to the second measurement input;
(iv) storing the obtained measurement data;
(v) repeating steps (ii)-(iv) after substituting at least one of the transmitting units performing the excitation with another transmitting unit from the transmitting units being coupled with the object and/or after substituting at least one receiving unit of the at least one of the measuring circuits performing the measurement with another receiving unit from the receiving units being coupled with the object;
(vi) connecting power ground of each receiving unit to the cold spot of the excitation unit, thus exciting the object and performing each measurement while connected to a common potential, and
(vii) inserting a reference element into one of the measuring circuits into between the cold spot of the excitation unit and one of the receiving units connected to the cold spot, and performing a measurement on said reference element simultaneously with the measurement of the complete response of the object to the excitation, and thereby obtaining a measurement data on said respective receiving unit connected to the cold spot shifted by an offset value representative of systematic and common phase errors, wherein the result of the measurement performed on said reference element is also stored.

15. The method according to claim 14, further comprising substituting one of the transmitting units and/or substituting at least one of the receiving units of at least one of the measuring circuits in a manner controlled by a multiplexer with scanning through the transmitting units and/or the receiving units.

16. The method according to claim 14, further comprising
    discretizing the object and representing the object by a directed graph obtained in network model approximation before initiating the measurement, and
    repeating steps (ii)-(iv) until achieving overdetermination of a system of equations for determining impedance values represented by branches of the directed graph, where unknowns of equations forming said system of equations are said impedance values and coefficients thereof are the measurement data obtained by measuring the complete response of the object to the excitation.

17. The method according to claim 14, further comprising performing the excitation of the object on different excitation frequencies for achieving the overdetermination of said system of equations.

18. The method according to claim 14, wherein the excitation of the object is also carried out with swapping the hot spot and the cold spot of the excitation unit on the transmitting units for achieving the overdetermination of said system of equations.

19. The method according to claim 14, wherein the reference element is a purely ohmic resistor and the method further comprises transforming the measurement data obtained by measuring the complete response of the object to the excitation into measurement data compensated for systematic and common phase errors by making use of the measurement data shifted by an offset value obtained by performing the measurement on the reference element.

20. The method according to claim 14, further comprising formatting the stored measurement data into a format suitable to be used directly by a soft-field tomography imaging algorithm through a preprocessing step.

21. The measuring system according to claim 3, wherein said reference element is provided by an element of purely ohmic resistance.

22. The measuring system according to claim 5, wherein the measuring units are lock-in amplifiers.

* * * * *